United States Patent [19]

Lauks

[11] Patent Number: 5,049,073
[45] Date of Patent: Sep. 17, 1991

[54] DEVICE FOR FASTENING A SET OF TEETH TO A JAWBONE OF A PATIENT

[76] Inventor: Nikola Lauks, Saalkamp 8, 2000 Hamburg 65, Fed. Rep. of Germany

[21] Appl. No.: 441,456

[22] Filed: Nov. 27, 1989

[30] Foreign Application Priority Data

Nov. 25, 1988 [DE] Fed. Rep. of Germany ....... 3839837

[51] Int. Cl.⁵ .................... A61C 8/00; A61C 13/28
[52] U.S. Cl. .................... 433/173; 433/169; 433/174
[58] Field of Search ................ 433/173, 174, 177, 169

[56] References Cited

U.S. PATENT DOCUMENTS

| | | | |
|---|---|---|---|
| 4,575,340 | 3/1986 | Lustig | 433/173 |
| 4,713,003 | 12/1987 | Symington et al. | 433/173 |
| 4,722,688 | 2/1988 | Lonca | 433/173 |
| 4,756,689 | 7/1988 | Lundgren et al. | 433/173 |
| 4,787,848 | 11/1988 | Ross | 433/174 X |
| 4,850,870 | 7/1989 | Lazzara et al. | 433/174 |
| 4,854,872 | 8/1989 | Detsch | 433/174 X |
| 4,854,873 | 8/1989 | Linden | 433/173 |
| 4,927,363 | 5/1990 | Schneider | 433/169 X |
| 4,950,161 | 8/1990 | Richter | 433/169 |

Primary Examiner—Robert P. Swiatek
Assistant Examiner—Nicholas D. Lucchesi
Attorney, Agent, or Firm—Herbert Dubno

[57] ABSTRACT

A device for retaining a tooth set such as a bridge in the mouth of a patient has an implant with an anchor end received in a drilled cavity in the jaw and provided with longitudinal flutes. On the crown anchor at the opposite end of this implant, a two-part crown can be provided. The primary crown part is connected to the crown carrier by a screw and has an external taper onto which the secondary crown part can be applied with adhesive friction. The secondary crown part is anchored in the artificial tooth set.

37 Claims, 3 Drawing Sheets

DEVICE FOR FASTENING A SET OF TEETH TO A JAWBONE OF A PATIENT

CROSS REFERENCE TO RELATED APPLICATION

This application is related to my copending application Ser. No. 07/304,365 now U.S. Pat. No. 4,998,881, filed 30 Jan. 1989.

FIELD OF THE INVENTION

My present invention relates to a device for fastening a set of teeth in a jaw of a human patient and, more particularly, to a device for this purpose which includes at least one implantable member or implant and a crown on the set of teeth to be affixed to that implant.

BACKGROUND OF THE INVENTION

Conventional systems for anchoring a set of teeth, for example a bridge in the bones of the jaw of the patient, generally require relatively large anchor members which may be sunk in the bones and for which a corresponding cavity in the bone must be fabricated in a substantially freehand manner. The anchor members have a rough upper surface and several discontinuities to facilitate the growth of bone tissue into the implant during the healing process so as to ensconce the implant in the bone.

The spaces between the implant and the surrounding spongiosa are highly prone to infection. Furthermore, since the freehand implantation method makes the size of this space difficult to control, the risk factor for infection is particularly great in earlier systems.

In practice, the conventional anchor has a diameter of about 4 mm so that insertion of the implant using prior art techniques into bones of limited width in the jaw is excluded.

With the aid of a spacer disk, the implant of the prior art systems can be provided with a crown of a set of teeth to be affixed to the jaw, the crown being attached by a screw to the implant. The screw usually must pass through the tooth set and project into the implant. Any discontinuity in the tooth set resulting from the insertion or presence of the screw must be filled. As a consequence, the artificial tooth is generally mounted in a nonremovable manner on the jaw. The tooth set cannot be readily removed, e.g. for cleaning.

Another drawback of earlier systems for mounting a tooth set of a patient on the jaw is that the chewing movements of the patient tend to loosen the screw so that the crown and implant tend to separate and the set of teeth can loosen in the mouth of the patient. To obviate this disadvantage, it is frequently necessary for the dentist or prosthetist to drill through the set of teeth in the region of the screw so that the screw can be tightened. This, of course, requires repair of the damaged set of teeth in the mouth of the patient.

OBJECTS OF THE INVENTION

It is the principal object of the present invention to provide an improved device for anchoring a set of teeth in the mouth of a patient whereby the drawbacks of earlier systems are avoided.

Another object is to provide a device of the type described which allows expedited healing of the implant and knitting thereof into the bone of the patient, as permanent, hygienic and reliable attachment of the set of teeth in the mouth of the patient and improved patient comfort even during chewing movements.

Still another object of the invention is to provide an improved device for the attachment of a set of teeth in the mouth of the patient whereby removal is possible, but retention during chewing movements is reliably ensured when the set of teeth is in place.

SUMMARY OF THE INVENTION

These objects and others which will become more readily apparent hereinafter are attained, in accordance with the present invention, by providing an implant adapted to be anchored in a jawbone of a human subject so that its end turned away from the bone is formed with a crown carrier and the crown adapted to be mounted on this carrier is comprised of two parts of which one part forms the primary crown and the other part forms a secondary crown. The primary crown is fastened to the crown carrier while the secondary crown is seated on the primary crown in a defined position.

More specifically, the device of the present invention comprises:

an elongated implant adapted to be fitted into a bore in a bone of a human jaw and having an implanted end received in said bore and an opposite end formed as a crown carrier;

a two-part crown mounted on the crown carrier and comprising:

a primary crown part abutting the crown carrier, a secondary crown part fitting onto the primary crown part and secured to the set of teeth, and means between the parts defining a predetermined orientation of the secondary crown part relative to the primary crown part upon fitting of the secondary crown part onto the primary crown part; and means for securing the primary crown part to the crown carrier.

It is thus possible to initially seat the implant in a jawbone of the patient and permit bone growth and healing to occur whereupon, after the healing process, the primary crown can be connected by a screw connection to the implant.

As a result of the perfect fitting of the secondary crown onto the primary crown, i.e. the close fit between them, the secondary crown can then be slid over the primary crown and affixed with a sufficient adhesive friction thereto in a well defined position, the frictional adhesion being sufficient to prevent any removal of the secondary crown from the primary crown by other than an extraordinary pulling movement of the type necessary for removal of the bridge for cleaning.

It is possible to fabricate the implant, the primary crown and the secondary crown industrially and commercially by mass production techniques, since only the secondary crown need be accommodated in the tooth set which is to be mounted in the mouth. Only the tooth set is individual to the patient.

Since only the primary crown is connected by a screw to the implant, and the secondary crown on the primary crown is fastened on the primary crown only by adhesive friction, it is possible to remove the tooth set, e.g. the bridge, from the mouth of the patient for cleaning purposes and after cleaning to reset the tooth set in the mouth of the patient.

According to an important feature of the invention, the implant has a generally cylindrical to slightly conical anchoring part which can be lodged in the bone and has flutes extending generally in its longitudinal direction. These flutes give rise to a significant increase in the surface area of the anchor part which makes it possible to reduce the diameter of the anchor part and yet permit sufficient growth of the bone tissue into the flutes and around the anchor part to enable the anchor part to be retained firmly in the bone and, of course, to permit the spongiosa to grow against the implant and thus minimize the incursion of infectious microorganisms.

Upon insertion of the implant in the drilled cavity provided therefor in the bone, residual air and blood can flow out through the flutes, thereby greatly reducing the danger of infection.

In addition, the system of the invention avoids the development of static pressure which could result from a damming-up of the blood and air mixture of the drill hole during insertion of the implant and which might interfere with the insertion or cause pain or discomfort to the patient.

According to another feature of the invention, the implant is provided at its side turned toward the crown with a radially outwardly extending flange which is received in a recess specifically provided for this flange in the jawbone in the region of the compacta. Since the annular flange is received in a correspondingly shaped and dimensioned recess in the compacta, the intracapillary space between the implant and the drill cavity is closed off from the environment to prevent the incursion of infectious microorganisms.

This is supported by the intact mucous membrane which, in a natural manner after implantation, closes over the bone covering parts of the implant.

According to a further feature of the invention, the crown carrier is disposed at a spacing from the annular flange and is resiliently connected with the implant.

In this manner, the mechanical loading between the implant and the bone tissue surrounding the implant can be reduced. This is because the compression and shear forces which constitute the load during chewing movements are not directly transmitted from the implant to the bone tissue because the resilience of the intramobile element of the implant which forms the resilient connection is very much greater than the resilience of the gum tissue. As a consequence, the junction between the implant and the bone tissue will be stressed only with the limits of the physiological composite with the residual pressure or force being taken up transmitted via the contact surface of the tooth set with the gum tissue and transmitted thereby to the jaw bone.

Because of the resilience of the intramobile element of the implant, the compressive forces are not transmitted directly or fully to the implant body as is the case in rigid implants. This greatly increases the life of the implant.

BRIEF DESCRIPTION OF THE DRAWING

The above objects, features and advantages of my invention will become more readily apparent from the following description, reference being made to the accompanying highly diagrammatic drawing in which.

SPECIFIC DESCRIPTION

Figure 9:
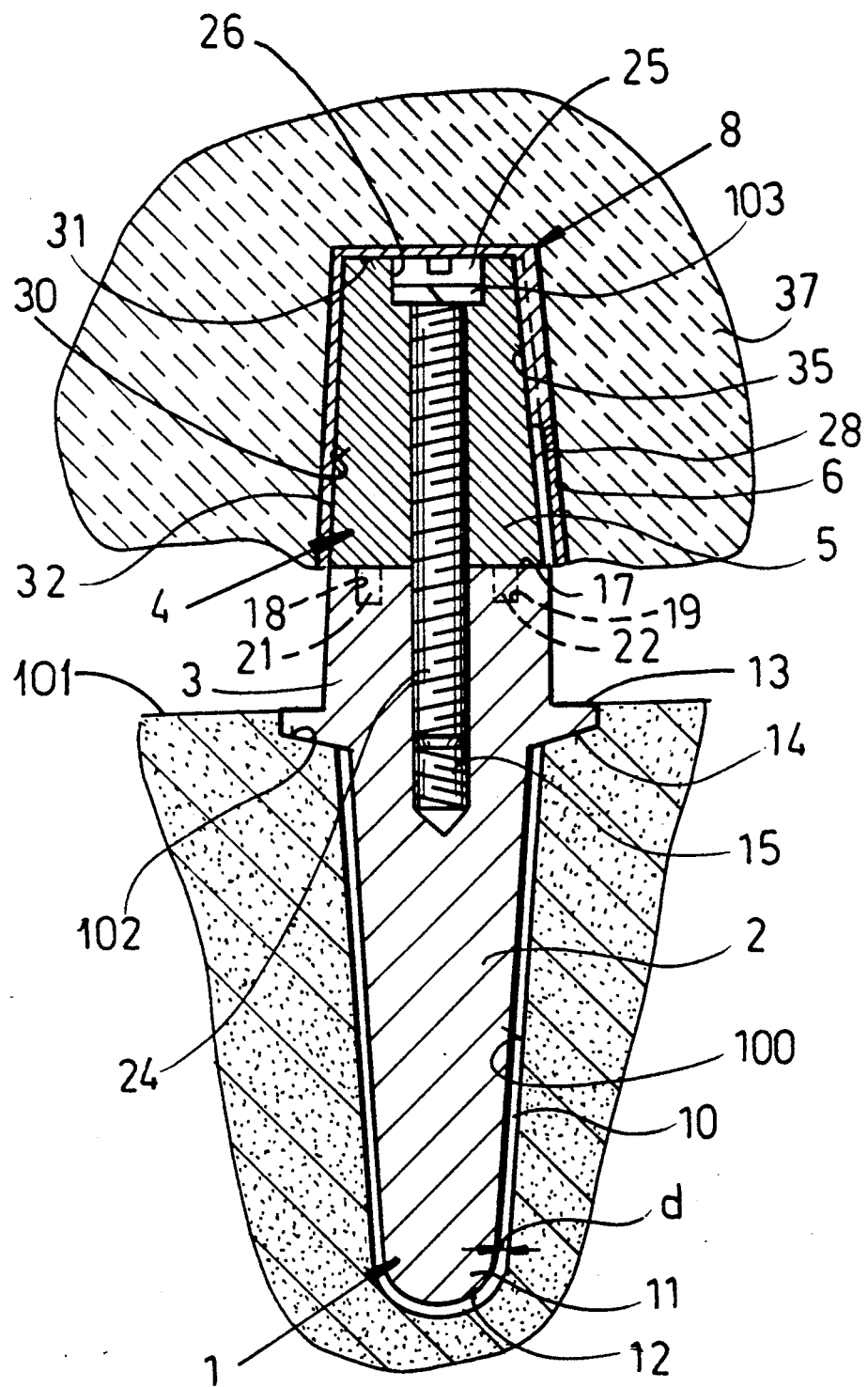
FIG. 9 is a cross-sectional view illustrating the device of the invention.

The device for fastening a set of teeth in the mouth of a patient comprises an implant 1 which can be fitted into a cavity 100 formed by the drill 38 in a jawbone 101 of a patient (see FIG. 9). At its end 2 turned away from the jawbone, the implant 1 is formed with a screw carrier 3 on which a crown 4 can be supported.

The crown 4 comprises two parts 5 and 6, the first of which is a primary crown 7 and the other of which is the secondary crown 8 (see FIGS. 1, 4, 7 and 10).

The implant 1 comprises a cylindrical to slightly conically shaped anchoring part 9 which is formed with flutes 10 extending radially into the part 9 and are substantially uniformly distributed around the anchor part 9, i.e. are substantially angularly equispaced therearound.

The flutes 10 are sunk to a depth d of about 0.1 mm below the remaining outer surface of the anchor part 9. The anchor part 9 can have a diameter of 2.5 to 3.8 mm and preferably a length of 7 to 13 mm.

As it is extremely remote from the crown carrier 3 and lodged most deeply in the bone, the end of the anchor part 9 is rounded at 12.

Figure 1:
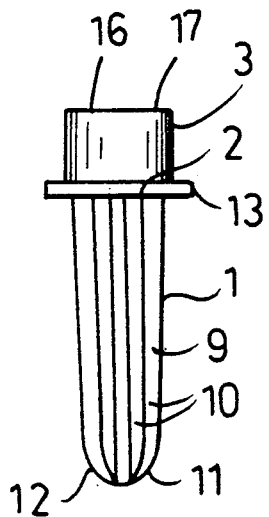
FIG. 1 is a side elevational view of the implant of the device of the invention.
Figure 2:
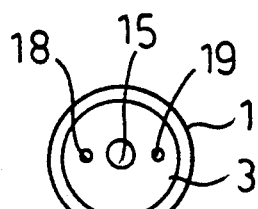
FIG. 2 is a plan view of the implant of FIG. 1.
Figure 3:
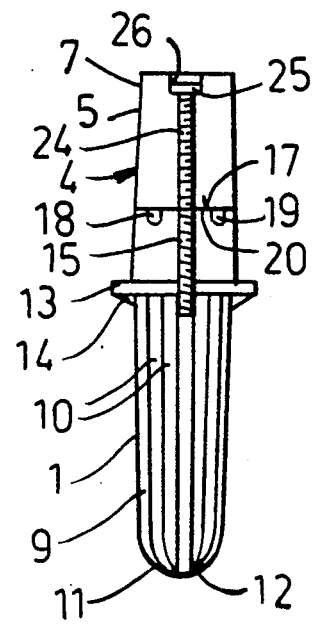
FIG. 3 is a side elevational view of the implant onto which a primary crown has been mounted in accordance with the invention.
Figure 4:
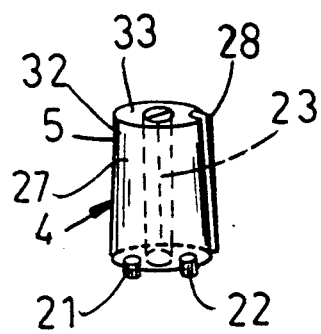
FIG. 4 is a perspective view of the primary crown as seen from a side.
Figure 5:
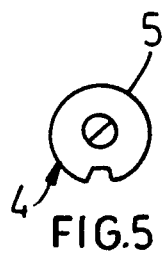
FIG. 5 is a top plan view of the primary crown of FIG. 4.
Figure 6:
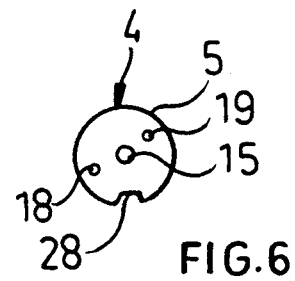
FIG. 6 is a bottom plan view of the primary crown of FIG. 4.
Figure 7:
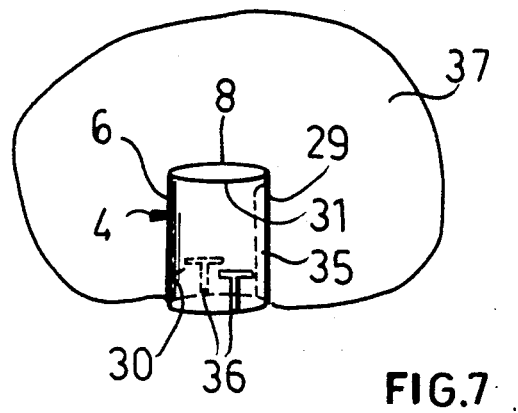
FIG. 7 is a side elevation view in perspective of a secondary crown according to the invention.
Figure 8:
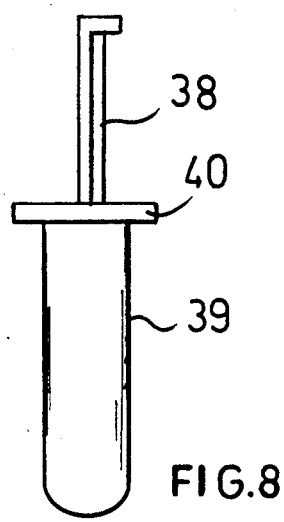
FIG. 8 is an elevational view of an end drill for making the drilled cavity for the implant of FIG. 1.

At the end of the anchor part 9 turned away from the rounded extremity 12, the anchor part is formed with a radially outwardly projecting annular flange 13. The annular flange 13 which is slightly conical at its underside, can be received in a recess 102, especially formed for this purpose by the bone drill of FIG. 8.

At the upper side of the annular flange 13 the crown carrier 3, which is substantially cylindrical, projects upwardly. The crown carrier is preferably highly polished, i.e. provided with a bright finish and is formed with an internally threaded bore 15 which extends along its longitudinal axis and projects into the anchor part 9.

The crown carrier 3 is formed at its side 16 turned away from the annular flange 13 with a support face 17 abutting the primary crown 7. The crown carrier is also provided in the region of the support face 17 with two blind bores 18 and 19 which are disposed adjacent the threaded bore 15. The primary crown is affixed to the crown carrier 3. The primary crown 7 has an abutment surface 20 which is matched to the support surface or face 17. In a direction turned away from the abutment surface 20, the primary crown 7 conically converges slightly, i.e. is tapered.

From the abutment surface 20 of the primary crown, two guide pins 21 and 22 project and are formfittingly received in the blind bores 18, 19 of the crown carrier 3.

The primary crown 7 is provided with a bore 23 registering with the threaded bore 15 in the crown carrier and through which a clamping screw 24 extends to engage the thread of the bore 15. The clamping screw 24 is formed with a head 25 which is received in a recess 26 of the primary crown 7. Below the head 25 a locking washer 103 of the split-washer type is provided to prevent self-loosening of the screw 24.

The primary crown 7, in the region of its peripheral surface 27, is formed with a guide groove 28 which extends generally in the same direction as the locking screw 24.

The secondary crown 8 is formed as a hood closely fitted to the primary crown 7 and its internal surfaces 30 and 31 are matched to be complementary to the external surfaces 32 and 33 of the primary crown 7 in the sense that, once the secondary crown is placed upon the primary crown, the two parts are retained together by adhesive friction.

The secondary crown in the region of its conical or tapering inner surface 30 is provided with a guide rib 35 which matches the guide groove 28 of the primary crown and is parallel thereto The guide rib 35 and the guide groove 28 engage in a solid connection to permit the secondary crown to be placed over the primary crown in only one predetermined position.

The secondary crown 8 in the region of its open side turned toward the annular flange 13 is provided with retaining notches 36 engaged by the material of the tooth set 37 which fits these notches and thereby anchors the secondary crown part 8 in the tooth set 37.

The guide rib 35 is active in the sense that it can have a widened portion or a constricted portion to vary the adhesive friction between the secondary crown 8 and the primary crown 7.

To fabricate the implant, cavity or bore, an end drill 38 is provided and can have a boring crown 39 whose shape and dimensions match those of the anchor part 9. The end drill 38 is also provided with a milling plate 40 whose dimensions correspond to the annular flange 13.

The device of the invention is used as follows:

Utilizing the end drill 38 and the boring device for surgical jaw implant cavities described in German Patent Application 38 32 823, one or more precise and mutually parallel implant cavities are drilled in a jawbone of the patient, the milling plate 40 further sinking recesses in the compacta to accommodate the flange 13.

The implants 1 are thus fitted snugly in the cavities so that their anchor parts 9 are close-fittingly engaged in the recess and the flange is received in the recess formed at the end of the cavity.

Any air or blood residues within the cavity are permitted to escape by passage through the flutes 10 to the exterior.

When the flange 13 enters the respective recess 102, it forms a bone closure part which prevents microorganisms from penetrating along the anchor part 6 into the cavity and thereby eliminates possible infection.

After the growth of the bone tissue into the flutes of the implant 1 and healing of the implant in place, the gum flesh with its mucous membrane grows over the flange 13 to completely seal the implant against the exterior.

After healing of the implant 1, the primary crown 7 can be connected to the crown carrier 3 by the screw 24. In this case, the primary crown 7 has its abutment surface 20 fitted onto the support surface 17 and the guide pins 21 and 22 of the primary crown inserted into the blind bores 18 and 19 of the crown carrier 3.

The screw 24 is passed through the bore 23 and threaded into the bore 15 of the crown carrier and into the anchor part 9 until the head 25 of the screw 24 is fully received in the recess 26 and locks against the lock washer 103.

The pins 21 and 22 engaging in the blind bores 18 and 19 fix the orientation of the crown with absolute precision relative to the implant and likewise absolutely secure the primary crown against rotation relative to the crown carrier so that during chewing movements of the patient, the screw 24 does not loosen.

After the primary crown 7 is affixed to the crown carrier 3, the secondary crown 8 to which the tooth set 37 is attached, can be shoved onto the primary crown 7. The tooth set 37 is usually a bridge or the like.

During this movement, the inner surfaces 30 and 31 of the secondary crown come into close fitting contact with the other surfaces 32 and 33 of the primary crown so that below these surfaces, an adhesive friction is generated which retains the bridge in place.

During the sliding of the secondary crown 8 onto the primary crown 7, the guide rib 34 on the inner surface of the secondary crown is fitted into the groove of the primary crown to ensure a precise orientation of the secondary crown on the primary crown with repeated removals and replacements of the tooth set. This is especially important when a plurality of implants 1 are fastened in the jaw of the patient with the absolute parallelity ensured with the drilling device of the above-mentioned German Patent Document 38 02 789.

Figure 10:
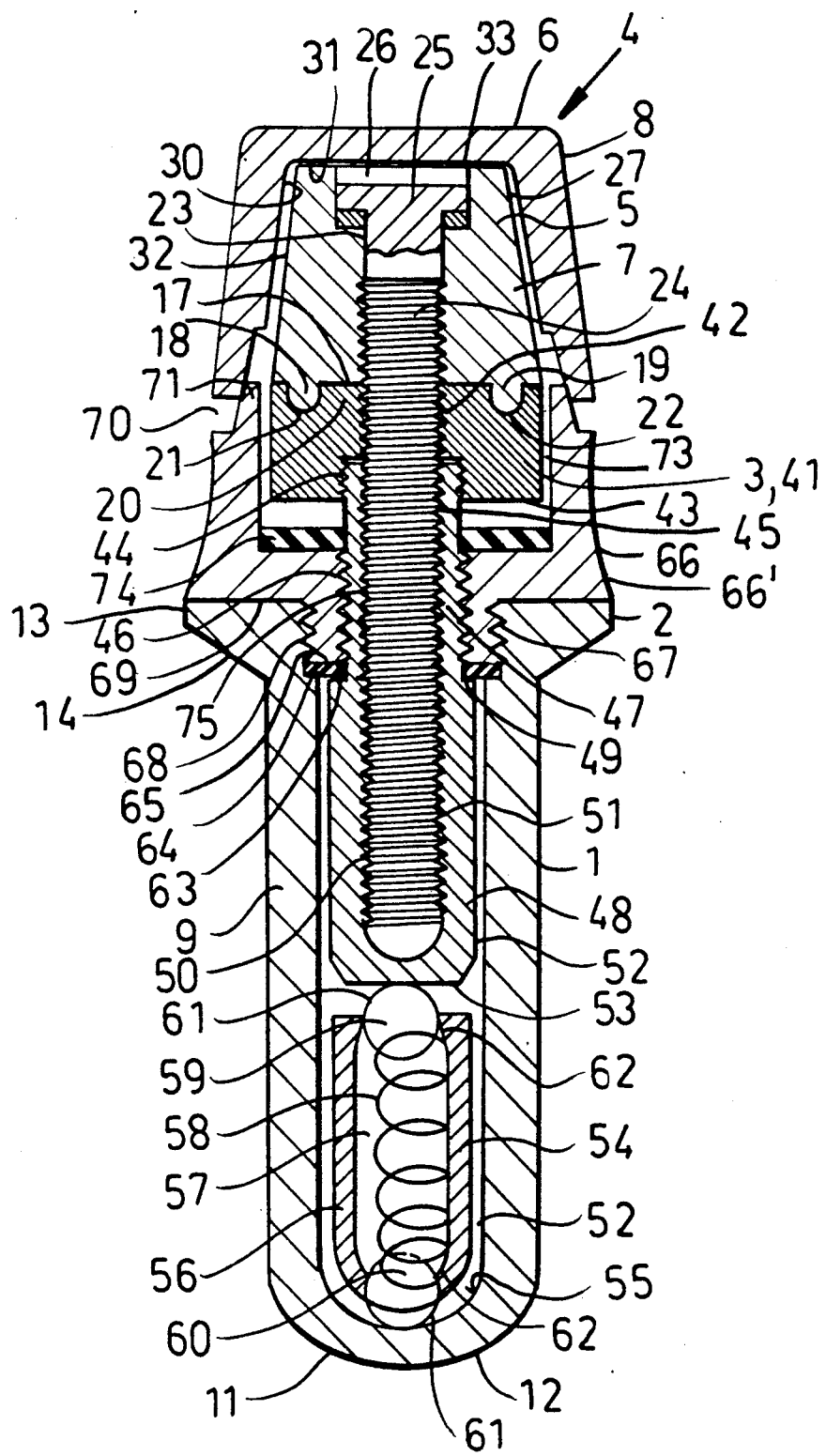
FIG. 10 is a cross sectional view of an implant showing the use of primary and secondary crowns and an intramobile element for absorbing some of the compressive forces resulting from chewing movements.

Referring to FIG. 10, in which reference numerals identical to those of the preceding Figures are used to identify similarly functioning parts, it can be seen that the crown carrier 3, 41 can be spaced from the annular flange 13 of the implant and resiliently connected to the implant 1.

The crown carrier 3, 41 here comprises a substantially cylindrical body formed with a bore 42 substantially along its axis and through which the tightening screw 24 can pass. On the underside 43, the crown carrier 3, 41 is provided with an annular recess 44 radially outwardly of the screw 24 and surrounding same. This recess is formed with an internal thread 45 in which the outer screw thread 46 of a shaft 47 is screwed. This shaft 47 forms part of an implant pin 48.

The implant pin 48 and the shaft 47 are substantially cylindrical of the diameter of the shaft 47 being less than that of the remainder of the implant pin 48.

The implant pin 48 has its screw thread 51 extending from the screw thread 50 in an extension of the bore 49. The screw 24 is thus threaded into the bores in the shaft 47 and the pin 48.

The implant 48 is held against rotation, e.g. by a groove and rib arrangement or some other key-type connection, in a space 52 within an anchoring part 9 of the implant 1 in which it is axially movable.

The chamber 52 extends practically the full length of the implant 1 to terminate close to its rounded end 12. The implant pin 48 at its end 53 opposite the shaft 47 engages a resilience-generating structure 54 in the form of a sleeve or body slidable within the chamber 52 and stressed between the end 53 of the pin 48 and a floor 55 of the chamber 52 of the anchoring part 9 of the implant 1. The resilience body 54 comprises a sleeve 56 whose outer dimensions correspond substantially to the inner dimensions of the chamber 52 in which it is received and which defines, in turn, a substantially cylindrical inner space 56 in which a compression spring 58 is provided.

The compression spring 58 is braced between two balls 59 and 60 having surfaces 61 projecting above and below the sleeve 56. The balls 59 and 60 are held against escape from the sleeve by constrictions 62 of the latter. These constrictions reduce the cross section of the inner space 57 at the ends of the sleeve.

The implant pin 48 is provided at its end turned toward the shaft 47 with an annular abutment flange or shoulder 63 adapted to engage a rubber washer 64 which is disposed upon an abutment surface or end 65 of an implant spacer screw 66.

This implant spacer screw 66 is formed with a boss 67 having an external screw thread threaded into an internal screw thread 68 in the anchor part 9 of the implant 1 in the region of its annular flange 13.

The implant spacer screw 66 comprises an abutment surface 69 which is turned toward the annular flange 13 and is adapted to engage the latter.

The implant spacer screw 66 has an outer surface 66' which is flush with the outer surface of the flange and substantially conically converges in the direction of the crown carrier, i.e. the direction turned away form the annular flange 13. The surface 66' is also formed at its end remote from the flange 13 with an annular recess 70 defining an annular collar 71.

The collar 71 is fitted to engage snugly in a complementary annular groove 72 of the secondary crown 8, the shapes and dimensions being such that the collar 71 sealingly and slidingly is received in the annular groove 72.

The implant spacer screw 66 is also provided with a central recess 73 which extends partway through this screw and is dimensioned to slidingly receive the crown carrier 3, 41. At the bottom of this recess, forming a stop for the underside 43 of the crown carrier 3, 41, a rubber washer 74 is provided.

The implant spacer screw 66 is also provided with a central bore 49 in which the shaft 47 of the implant pin 48 is slidingly received.

The device illustrated in FIG. 10 is mounted in the following manner:

After the bore or cavity in the jawbone has been prepared in the manner described previously, the anchoring part set of the implant 1 is inserted and the bone tissue allowed to heal in place. During this period, the space 52 remains empty, but is closed off by a plug which is threaded like the spacer screw 66 into the anchor part 9.

After healing, the plug is removed and the annular flange 13 is exposed for fastening the crown on the implant.

First the resilience body 54 is placed in the chamber 52 and then the implant pin 48 with its shaft 47 received in the spacer body 66 and threaded at 45 to the crown carrier 3, 41 is inserted in the implant and joined thereto by the screw connection 67, 68.

The dimensions of the pin 48 are so selected that it resiliently bears against one of the balls 59 while the other ball 60 resiliently bears against the floor 55 while the shoulder 63 is held with a predetermined pressure generated by the spring 58 against the rubber washer 54.

The primary crown 7 is then mounted in place by the screw 24 on the crown carrier 3, 41, prior to which the screw has been lubricated with petrolatum.

The secondary crown, connected with a set of teeth 37 can then be placed on the primary crown in the manner described. Between the collar 71 and groove 72 a resilient spacing is provided which allows, also lubricated by petrolatum if desired, the resilient connection between the crown 4 and the implant 1.

Upon the application of pressure by the dental prosthesis, the compression is taken up by the resilience body 54 until the underside 43 of the crown carrier 41 abuts the rubber washer 74. Upon relief of pressure, the crown moves upwardly until the shoulder 63 engages the rubber washer 64.

The rubber washer 64 and 74 serve to dampen the extreme positions of the crown and further reduce the strain on the implant.

I claim:

1. A device for fastening a set of teeth on a human jaw, comprising:

an elongated implant for a bore in a bone of a human jaw and having an implanted end received in said bore and an opposite end formed as a crown carrier, said implanted end having a rounded extremity lodged in said bone, said implanted end, at an extremity turned toward said crown carrier, being formed with a flange projecting radially outwardly, said flange having an underside turned toward said rounded extremity and conically converging in a direction thereof, said implant including an anchor portion adapted to be fitted into said bore and said crown carrier being spaced from said flange and resiliently connected with said implant, said crown carrier being formed from a substantially cylindrical body;

a two-part crown mounted on said crown carrier and comprising:

a primary crown part separable from and abutting said crown carrier, a secondary crown part fitting onto said primary crown part and securable to said set of teeth, and means for securing said primary crown part to said crown carrier, said securing means being a screw received in a bore of said crown carrier that extends centrally therealong, said screw traversing said crown carrier, said crown carrier being formed on a side turned toward said anchor portion with an annular recess surrounding said screw and extending partly into said crown carrier; and an annular rubber washer surrounding said screw positioned between a face of said anchor portion and a surface of said crown carrier turned toward said anchor portion and radially interior of said outwardly projecting flange and an implant spacer threaded into said anchor portion adjacent said flange, said implant spacer having a recess receiving said washer and said crown carrier.

2. The device defined in claim 1 wherein said implanted end of said implant is elongated in a shape selected from the group consisting of cylindrical and of slightly conically tapered away from said crown carrier, and said implanted end is formed with longitudinally extending flutes along substantially a full length thereof.

3. The device defined in claim 2 wherein said flutes are generally radial and are substantially uniformly angularly equispaced around said implanted end.

4. The device defined in claim 3 wherein said flutes have a depth of about 0.2 mm.

5. The device defined in claim 4 wherein said implanted end has a rounded extremity lodged in said bone.

6. The device defined in claim 1 wherein said crown carrier is highly polished and is formed generally along an axis thereof with a threaded bore receiving a screw and forming part of said means for securing.

7. The device defined in claim 6 wherein said threaded bore extends into said implanted end.

8. The device defined in claim 1 wherein said crown carrier is formed at an extremity thereof turned away from said implanted end with an abutment surface engageable with said primary crown part, and a threaded bore opening at said surface substantially along an axis of said implant.

9. The device defined in claim 8 wherein said crown carrier is formed substantially in the vicinity of said threaded bore with a pair of blind bores.

10. The device defined in claim 9, further comprising means on said primary crown part engageable in said blind bores for orienting said primary crown part on said crown carrier.

11. The device defined in claim 10 wherein said primary crown part is formed with an engagement surface matched to said abutment surface and engaging same, said primary crown part tapering conically slightly away from said engagement surface.

12. The device defined in claim 11 wherein said means engageable in said blind bores comprises a pair of pins projecting from said engagement surface and each received formfittingly and snugly in a respective one of said blind bores.

13. The device defined in claim 12 wherein said primary crown part is formed with an axial bore registering with said threaded bore and traversed by a clamping screw threaded into said threaded bore, forming a means for securing and pressing said engagement surface against said abutment surface.

14. The device defined in claim 13 wherein said clamping screw has a head and said primary crown part is formed with a recess receiving said head.

15. The device defined in claim 14 wherein said primary crown part is formed along a peripheral surface thereof with an outwardly open guide groove extending generally in the same direction as said clamping screw.

16. The device defined in claim 15 wherein said secondary crown part is formed as a hood fitted over and onto said primary crown part and having internal surfaces matched to external surfaces of said primary crown part.

17. The device defined in claim 16 wherein said internal surfaces are matched to said external surfaces so as to generate sufficient friction therebetween to retain said secondary crown part on said primary crown part exclusively by said friction even upon chewing movements of the jaw.

18. The device defined in claim 17 wherein said inner surfaces of said secondary crown part are formed with a guide rib complementary to said groove and parallel thereto so that said rib fits into said groove.

19. The device defined in claim 18 wherein said rib and said groove form a slide joint constituting said means defining a predetermined orientation of said secondary crown part relative to said primary crown part.

20. The device defined in claim 19 wherein said rib is formed so as to be active in varying the adhesion friction of the secondary crown part with respect to the primary crown part.

21. The device defined in claim 20 wherein said hood has outer surfaces securable to said set of teeth and said set of teeth is a bridge.

22. The device defined in claim 21 wherein said outer surfaces have retention notches in which said set of teeth is anchored to said secondary crown part.

23. The device defined in claim 1 wherein said implant further comprises an implant pin receivable in said anchor portion and formed with a shaft having an outer screw thread received in an internal screw thread of said recess.

24. The device defined in claim 23 wherein the implant pin and said shaft are formed in one piece and are substantially cylindrical with the diameter of said shaft being smaller than the diameter of said implant pin.

25. The device defined in claim 24 wherein said shaft has a throughgoing bore provided with an internal screw thread threadedly engaged with said screw and said pin is formed with an extension of said bore of said shaft threadedly engaging said screw.

26. The device defined in claim 25 wherein said pin is nonrotatably but longitudinally shiftable in a space formed in said anchor portion and extending therein substantially to said rounded extremity.

27. The device defined in claim 26, further comprising a resilience body received in said space and braced against said pin and a floor of said space adjacent said rounded extremity.

28. The device defined in claim 27 wherein said resilience body comprises a sleeve shaped and dimensioned substantially to fit said space and having a substantially cylindrical interior, a compression spring in said interior, and a pair of balls pressed outwardly from said sleeve by said compression spring so that outer surfaces of said balls project outwardly beyond said sleeve against said floor and said pin, respectively.

29. The device defined in claim 28 wherein said interior of said sleeve is constricted at said ends to hold said balls in said sleeve.

30. The device defined in claim 29 wherein said pin has an annular shoulder at an end thereof from which said shaft extends forming an abutment.

31. The device defined in claim 30, further comprising a second annular rubber washer engageable by said shoulder and forming a stop for said pin in said anchor portion, said implant spacer having a screw end threaded into said anchor portion to hold said washer in place.

32. The device defined in claim 31 wherein said implant spacer has an externally threaded boss engaging an internal screw thread formed in said anchor portion adjacent said annular flange.

33. The device defined in claim 32 wherein said implant spacer is provided with an abutment surface turned toward and engageable with said flange as said spacer is tightened into said anchor portion.

34. The device defined in claim 33 wherein said spacer has an external surface tapering away from said flange.

35. The device defined in claim 34 wherein said external surface is provided at its end remote from said flange with an outwardly open annular recess defining an annular collar.

36. The device defined in claim 35 wherein said secondary crown part is formed with an internal recess complementary to said collar and forming a sliding fit therewith.

37. The device defined in claim 36 wherein said implant spacer has a central bore in which said shaft is slidably received.

* * * * *